(12) United States Patent
Ghosh et al.

(10) Patent No.: US 11,918,384 B2
(45) Date of Patent: *Mar. 5, 2024

(54) TEMPLATE-BASED ANALYSIS AND CLASSIFICATION OF CARDIOVASCULAR WAVEFORMS

(71) Applicant: KONINKLIJKE PHILIPS N.V., Eindhoven (NL)

(72) Inventors: Erina Ghosh, Boston, MA (US); Cristhian Potes, Salem, NH (US); Richard Earl Gregg, Westford, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 214 days.

This patent is subject to a terminal disclaimer.

(21) Appl. No.: 17/407,541

(22) Filed: Aug. 20, 2021

(65) Prior Publication Data
US 2022/0313169 A1 Oct. 6, 2022

Related U.S. Application Data

(63) Continuation of application No. 16/311,453, filed as application No. PCT/EP2017/064218 on Jun. 12, 2017, now Pat. No. 11,103,191.
(Continued)

(51) Int. Cl.
*A61B 5/0215* (2006.01)
*A61B 5/00* (2006.01)
(Continued)

(52) U.S. Cl.
CPC .......... *A61B 5/7221* (2013.01); *A61B 5/021* (2013.01); *A61B 5/0215* (2013.01);
(Continued)

(58) Field of Classification Search
CPC ................. A61B 5/0295; A61B 5/308; A61B 5/318–366; A61B 5/021–0235; A61B 5/02416; A61B 5/7246; A61B 5/7264
See application file for complete search history.

(56) References Cited

U.S. PATENT DOCUMENTS

2002/0188211 A1 12/2002 Voith
2011/0034812 A1 2/2011 Patangay et al.
(Continued)

FOREIGN PATENT DOCUMENTS

WO 9001895 A1 3/1990
WO 2007100276 A1 9/2007
(Continued)

OTHER PUBLICATIONS

W. Ali, L. Eshelman, M. Saeed, "Identifying Artifact in Aarterial Blood Prssure Using Morphogram Variabilty", Computers in Cardiology, pp. 697-700.
(Continued)

*Primary Examiner* — Thaddeus B Cox (57) ABSTRACT

In various embodiments, a first classification assigned to a periodic component of an electrical waveform that represents electrical activity in a patient's heart may be identified. A corresponding periodic component of a hemodynamic waveform that represents hemodynamic activity in the patient's cardiovascular system may be analyzed. The corresponding periodic component may be causally related to the periodic component of the electrical waveform. Based on the analysis, the previously-assigned classification may be assigned to the corresponding periodic component of the hemodynamic waveform in response to a determination, based on the analyzing, that the previously-assigned classification also applies to the corresponding periodic component. In a database of hemodynamic templates, a hemodynamic template associated with the previously-assigned
(Continued)

classification may be updated to include one or more features of the corresponding periodic component of the hemodynamic waveform.

13 Claims, 6 Drawing Sheets

Related U.S. Application Data

(60) Provisional application No. 62/353,139, filed on Jun. 22, 2016.

(51) Int. Cl.
*A61B 5/021* (2006.01)
*A61B 5/024* (2006.01)
*A61B 5/0295* (2006.01)
*A61B 5/346* (2021.01)
*A61B 5/35* (2021.01)
*A61B 5/352* (2021.01)
*A61B 5/364* (2021.01)
*A61B 5/366* (2021.01)

(52) U.S. Cl.
CPC ............ *A61B 5/0295* (2013.01); *A61B 5/346* (2021.01); *A61B 5/35* (2021.01); *A61B 5/352* (2021.01); *A61B 5/7246* (2013.01); *A61B 5/7264* (2013.01); *A61B 5/02416* (2013.01); *A61B 5/364* (2021.01); *A61B 5/366* (2021.01)

(56) References Cited

U.S. PATENT DOCUMENTS

| | | |
|---|---|---|
| 2012/0232416 A1 | 9/2012 | Gilham et al. |
| 2013/0023776 A1 | 1/2013 | Olde |
| 2013/0116580 A1 | 5/2013 | Liu |
| 2014/0180144 A1 | 6/2014 | Chen et al. |
| 2017/0311830 A1 | 11/2017 | Korzinov |

FOREIGN PATENT DOCUMENTS

| | | |
|---|---|---|
| WO | 2011080189 A1 | 7/2011 |
| WO | 2014055798 A1 | 4/2014 |

OTHER PUBLICATIONS

Aboukhalil, et al., "Reducing false alarm rates for critical arrhythmias using the arterial blood pressure waveform", Journal of Biomedical Informatics, Sience Direct, vol. 41, No. 3, Jun. 2008, pp. 442-451.

Li, et al., "Robust heart rate estimation from multiple asynchronous noisy sources using signal quality indices and a Kalman filter", Physiol Meas., Feb. 29, 2008, vol. 29 (1), 22 pages.

Sayadi, et al., "A Combined Dynamical Sequential Network for Generating Coupled Cardiovascular Signals with Different Beat Types", Applied Sciences and Communication Technologies, 2010 IEEE, pp. 1-5.

TEMPLATE-BASED ANALYSIS AND CLASSIFICATION OF CARDIOVASCULAR WAVEFORMS

TECHNICAL FIELD

The present application is a continuation of U.S. Pat. No. 11,103,191, which issued on Aug. 31, 2021, which is the U.S. National Phase application under 35 U.S.C. § 371 of International Application No. PCT/EP2017/064218 filed Jun. 12, 2017, which claims the benefit of U.S. Provisional Application No. 62/353,139 filed on Jun. 22, 2016. These applications are hereby incorporated by reference herein.

The present disclosure is directed generally to health care. More particularly, but not exclusively, various methods and apparatus disclosed herein relate to template-based analysis and classification of cardiovascular waveforms.

BACKGROUND

Cardiovascular waveforms representing arterial blood pressure ("ABP"), pulmonary artery pressure ("PAP"), central venous pressure ("CVP"), and plethysmography may be impacted by physiological changes such as ectopic beats and/or arrhythmias. In particular, electrical activity in a patient's heart, e.g., as measured by an electrocardiogram ("ECG"), may influence the shapes of these waveforms. A physician may then analyze the shape of these waveforms to identify abnormalities in the patient's heartbeat that warrants further investigation. However, the signal obtained by ECG and other devices is not perfect, noise and artifacts can be introduced which also affect the waveform shape. These shapes can sometimes be mistaken for abnormalities, even though they were introduced by the machine or other factor other than the patient's physiology.

SUMMARY

Algorithms for filtering and evaluating waveform quality sometimes incorrectly classify atypical electrical activity as noise or artifacts (e.g., due to interference and/or patient movement) when in fact the activity may evidence cardiovascular abnormalities. For example, some algorithms compare electrical and/or hemodynamic waveforms to templates of normal and abnormal waveforms. However, many abnormal waveforms may not match existing templates and may consequently lead to a noisy classification, when in fact a true cardiovascular abnormality exists. Thus, it would be beneficial to provide a method and system to analyze and classify cardiovascular waveforms in a manner that better identifies cardiovascular abnormalities and corroborates/refutes classifications made using existing algorithms.

The present disclosure is directed to inventive methods and apparatus for template-based analysis and classification of cardiovascular waveforms. For example, the present disclosure describes techniques for classifying (or annotating) periodic components of hemodynamic waveforms, such as heart beats, based on various signals such as templates of normal and abnormal waveforms, and/or for corroborating and/or reclassifying periodic components of electrical waveforms that represent electrical activity in patients' hearts. Moreover, templates associated with normal waveforms and various types of abnormal waveforms may be updated to include features of newly-identified normal and abnormal waveforms.

Generally, in one aspect, a method may include identifying a previously-assigned classification associated with a periodic component of an electrical waveform, wherein the electrical waveform represents electrical activity in a patient's heart; analyzing a corresponding periodic component of a hemodynamic waveform that represents hemodynamic activity in the patient's cardiovascular system, wherein the corresponding periodic component is causally related to the periodic component of the electrical waveform; assigning the previously-assigned classification to the corresponding periodic component of the hemodynamic waveform in response to a determination, based on the analyzing, that the previously-assigned classification also applies to the corresponding periodic component; and updating, in a database of hemodynamic templates, a hemodynamic template associated with the previously-assigned classification to include one or more features of the corresponding periodic component of the hemodynamic waveform.

In various embodiments, the method may further include: receiving electrophysiological data associated with the patient, wherein the electrophysiological data includes the electrical waveform and one or more previously-assigned classifications associated with one or more periodic components of the electrical waveform; and receiving hemodynamic data associated with the patient, wherein the hemodynamic data includes the hemodynamic waveform.

In various embodiments, the electrophysiological data is received from one or more electrodes of an electrocardiogram. In various embodiments, the hemodynamic data may include a signal indicative of arterial blood pressure of the patient. In various embodiments, the hemodynamic data may include a signal indicative of pulmonary blood pressure of the patient. In various embodiments, the hemodynamic data may include a signal indicative of central venous pressure. In various embodiments, the hemodynamic data may include a signal from a plethysmograph.

In various embodiments, the method may further include: identifying an unclassified periodic component of the same hemodynamic waveform or a different hemodynamic waveform associated with a different patient; matching the unclassified periodic component to a template of the database of hemodynamic templates; and assigning a classification associated with the matching template to the unclassified periodic component of the hemodynamic waveform. In various versions, the method may further include updating the matching template to include one or more features of the now-classified periodic component of the hemodynamic waveform.

In various embodiments, the previously-assigned classification may include an abnormal classification. The assigning may include assigning the abnormal classification to the corresponding periodic component of the hemodynamic waveform in response to a determination, based on the analysis, that a delta between the corresponding periodic component of the hemodynamic waveform and a previous periodic component of the hemodynamic waveform satisfies a threshold.

In various embodiments, the method may further include: identifying an artifact classification assigned to another periodic component of the electrical waveform deemed an artifact; analyzing another corresponding periodic component of the hemodynamic waveform that is causally related to the another periodic component of the electrical waveform; assigning an abnormal classification to the another corresponding periodic component of the hemodynamic waveform in response to a determination, based on the analyzing, that a delta between the another corresponding periodic component of the hemodynamic waveform and another previous periodic component of the hemodynamic waveform satisfies a threshold; and reclassifying the another periodic component of the electrical waveform with the abnormal classification.

In various embodiments, the previously-assigned classification may include a normal classification, and the assigning may include assigning the normal classification to the corresponding periodic component of the hemodynamic waveform in response to a determination, based on the analyzing, that the corresponding periodic component satisfies a signal quality index ("SQI").

In various implementations, the analyzing may include matching the corresponding periodic component to a template of the database of hemodynamic templates. In various versions, the updating may include coalescing the corresponding periodic component with a periodic component stored in association with the matching hemodynamic template.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the disclosure.

DETAILED DESCRIPTION

Cardiovascular waveforms such as those representing ABP, PAP, and/or CVP, as well as a signal from a plethysmograph ("PLETH") may be impacted by physiological changes such as ectopic beats and/or arrhythmias. In particular, electrical activity in a patient's heart, e.g., as measured by an ECG, may influence the shapes of various hemodynamic waveforms. Existing algorithms for filtering and evaluating waveform quality sometimes incorrectly classify atypical electrical activity as noise or artifacts when in fact the activity may evidence cardiovascular abnormalities. For example, some algorithms compare electrical and/or hemodynamic waveforms to templates of normal and abnormal waveforms. However, many abnormal waveforms may not match existing templates and may consequently lead to a noisy classification, when in fact a true cardiovascular abnormality exists. Thus, there is a need in the art to analyze and classify cardiovascular waveforms in a manner that better identifies cardiovascular abnormalities and corroborates/refutes classifications made using existing algorithms. More generally, it is recognized and appreciated that it would be beneficial to continuously learn new patterns associated with normal and abnormal cardiovascular waveforms. In view of the foregoing, various embodiments and implementations of the present disclosure are directed to classifying or annotating periodic components of cardiovascular waveforms, such as heart beats, based on various signals such as templates of normal and abnormal waveforms, and/or for corroborating and/or reclassifying periodic components of electrical waveforms that represent electrical activity in patients' hearts. Moreover, databases of templates of normal and abnormal waveforms may be updated to include features of newly-identified normal and abnormal waveforms.

Figure 1:
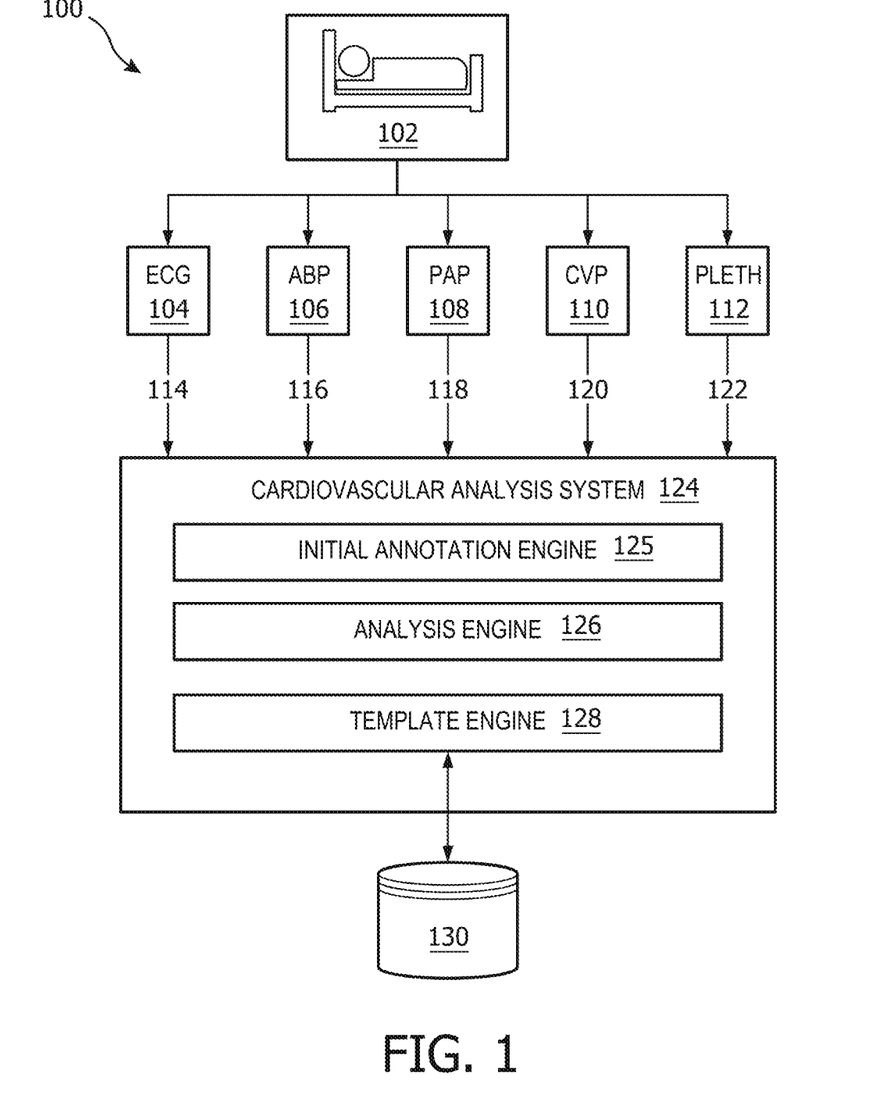
FIG. 1 illustrates an example environment in which disclosed techniques may be implemented, in accordance with various implementations.

Referring to FIG. 1, an example environment 100 is depicted in which disclosed techniques may be implemented. A patient 102 may be connected to various medical devices to monitor electrical activity in the patient's heart and/or hemodynamic activity in the patient's vascular system. For example, patient 102 may be monitored by one or more medical devices such as an ECG 104, an APB 106, a PAP 108, a CVP 110, and/or a PLETH 112. These devices are just examples and are not meant to be limiting. Other electrical and/or hemodynamic signals may be obtained and monitored.

In the case of the ECG 104, in some implementations, one or more electrodes (not depicted) may be affixed to patient 102 to detect electrical activity in the patient's heart to produce a signal 114. In the case of ABP 106, an instrument such as a sphygmomanometer may be used to measure ABP of patient 102, e.g., at regular intervals or continuously, to produce a signal 116. PAP 108 may take various forms, such a trans-thoracic echocardiogram ("TTE") and/or right heart catheterization, and may produce signal 118. In various embodiments, CVP 110 may be measured by connecting a central venous catheter (not depicted) to an infusion pump to produce signal 120. In the case of PLETH 112, a signal 122 may be produced by a plethysmograph, which is an instrument for measuring volume changes within an organ or whole body of patient 102.

In various embodiments, signals 114-122 may be provided to a cardiovascular analysis system 124. The operations performed by cardiovascular analysis system 124 may be distributed across multiple computer systems. For instance, cardiovascular analysis system 124 may be implemented as computer programs running on one or more computers in one or more locations that are coupled to each other through a network (not depicted). Cardiovascular analysis system 124 may include various engines and/or modules that may be implemented using hardware, software, or any combination of the two. In various embodiments, these modules and/or engines may include an initial annotation engine 125, analysis engine 126, and/or a template engine 128. In some implementations one or more of engines 125, 126 and 128 may be omitted. In some implementations all or aspects of one or more of engines 125, 126 and 128 may be combined. In some implementations, one or more of engines 125, 126 and 128 may be implemented in a component that is separate from cardiovascular analysis system 124.

Initial annotation engine 125 may be configured to analyze, in isolation, electrical signal 114 produced by ECG 104 for various characteristics. In some embodiments, initial annotation engine 125 may annotate various "periodic components" of an electrical waveform as "normal," "abnormal," or as an "artifact" (a.k.a. "noise"). As used herein, a "periodic component" of a waveform may refer to any component that typically occurs repeatedly in the waveform (though not necessarily identically from occurrence to occurrence). In some embodiments, the periodic component may be a recurring "peak" of the waveform. For example, in an electrical waveform, each "peak" may represent a surge in electrical activity. In other embodiments, the periodic waveform may refer to a "valley" or another typically recurring visual feature of the waveform such as a peak/valley pair (even though height or phase of the peak and depth of the valley may differ from occurrence to occurrence). The modifier "periodic" as used herein is meant to refer to the component being something that normally occurs periodically, or at the very least is supposed to occur periodically. It should be understood, however, that in various scenarios, particularly with severely ailing patients, a waveform produced by the patient may or may not exhibit the periodic components, and/or the periodic components may not actually occur periodically with a particular patient (this may or may not be a cause or result of the patient's ailment). In some embodiments, the annotations may be added by initial annotation engine 125 using various algorithms such as the Segment and Arrhythmia Analysis ST/AR ECG and/or DXL algorithms, although annotations may be added using other algorithms as well.

In various implementations, analysis engine 126 may be configured to analyze annotated waveforms representing electrical activity in a patient's heart and/or hemodynamic activity in a patient's vascular system to determine whether one or more annotations, or "classifications," are correct, incorrect, etc. In a hemodynamic waveform, each "peak" (or combination of peak and valley) may represent a heartbeat. In various implementations, analysis engine 126 may be configured to identify a classification/annotation assigned, e.g., by initial annotation engine 125, to a periodic component of an electrical waveform that represents electrical activity in a heart of patient 102. For example, analysis engine 126 may identify a particular peak that is classified or annotated as "normal," "abnormal," or as an "artifact." Analysis engine 126 may then analyze a corresponding periodic component of a hemodynamic waveform that represents hemodynamic activity in the patient's vascular system (e.g., representing one or more of signals 116-122). The corresponding periodic component may be causally related to the periodic component of the electrical waveform.

Based on the analysis, analysis engine 126 may classify (or reclassify if already classified elsewhere) the corresponding periodic component of the hemodynamic waveform with the same classification as was assigned to the periodic component of the electrical waveform or a different classification. For example, if analysis of the hemodynamic waveform corroborates a classification of "normal" assigned to a periodic component of the electrical waveform by initial annotation engine 125, then analysis engine 126 may classify the corresponding periodic component of the hemodynamic waveform as "normal." On the other hand, suppose the analysis contradicts an "artifact" classification assigned to the periodic component of the electrical waveform by initial annotation engine 125. For example, suppose analysis engine 126 determines using techniques described herein that the corresponding periodic component of the hemodynamic waveform actually indicates an abnormality. In such case, analysis engine 126 may classify the corresponding periodic component of the hemodynamic waveform as "abnormal," and may reclassify the periodic component of the electrical waveform from "artifact" to "abnormal."

In various implementations, once analysis engine 126 classifies and/or reclassifies a periodic component of an electrical and/or hemodynamic waveform, analysis engine 126 may effectively "update" its knowledge and/or the knowledge of cardiovascular analysis system 124. For example, in some embodiments, a template engine 128 may maintain one or more databases of hemodynamic templates. In various embodiments, each hemodynamic template may include one or more "features" of one or more periodic components of one or more hemodynamic waveforms with the same classification as the periodic component of the hemodynamic waveform. In FIG. 1, template engine 128 maintains a database 130 of hemodynamic templates that includes templates associated with a "normal" classification, as well as templates have various types of "abnormal" classifications associated with different ailments (e.g., ectopic beats, arrhythmias, etc.). However, this is not meant to be limiting. In other embodiments, templates classified as normal, abnormal, or even "artifacts," may be stored in separate databases.

After analysis engine 126 performs the analysis described above, in various embodiments it may request that template engine 128 update one or more of template databases 130 with one or more features of the corresponding periodic component of the hemodynamic waveform. Various features of periodic components of waveforms or the underlying hemodynamic activity may be used to update templates, ranging from comprehensive data representing the entire waveform, to specific features such as the maximum/minimum amplitude, distance from a prior peak, rate of increase/decrease, turbulence, blood density, mean velocity, blood viscosity, and so forth. In some embodiments, features of multiple waveforms (e.g., electrical and hemodynamic) may be added to a template. For example, "pulse transit time" may be a time difference between a peak of an ECG waveform and a valley of an ABP or PLETH waveform. In some embodiments, a pulse transit time may be included in a template as an annotation to a periodic component.

When new or otherwise unclassified hemodynamic waveforms are being analyzed by analysis engine 126, it may compare periodic components of the new hemodynamic waveforms with the templates in database 130. A template may match a particular periodic component under analysis when, for instance, one or more features of the periodic component under analysis are sufficiently similar to corresponding features of the template.

For example, in some embodiments, a feature vector may be extracted from the periodic component under analysis. Various machine learning techniques may be employed to calculate similarity measures between a template feature vector associated with the template and the feature vector of the periodic component under analysis. In some embodiments, mathematical models such as neural networks and/or logistical regression may be trained. Various learning algorithms for training such models may be used such as, for example, batch or stochastic gradient descent and/or application of the normal equations. If the calculated similarities satisfy one or more thresholds, there may be a match. Consequently, the periodic component under analysis may be classified the same as the template feature vector. In some implementations, one or more features from the feature vector extracted from the periodic component may be incorporated into a template of template database 130, e.g., to aid in future comparisons.

In other embodiments, a hemodynamic template may include one or more periodic components that, for instance, represent a coalescing of a plurality of previously-classified periodic components. The periodic component under analysis may be correlated to the one or more periodic components of the template to determine whether there is a match (e.g., if a difference between the two satisfies or fails to satisfy one or more thresholds). In some embodiments, the periodic component under analysis may be subtracted from the template periodic component(s), and the difference may be compared to the one or more thresholds. In other embodiments, techniques such as Fast Fourier Transforms ("FFT") or covariance shifting may be employed to correlate the periodic component under analysis to the template periodic component.

Figure 2:
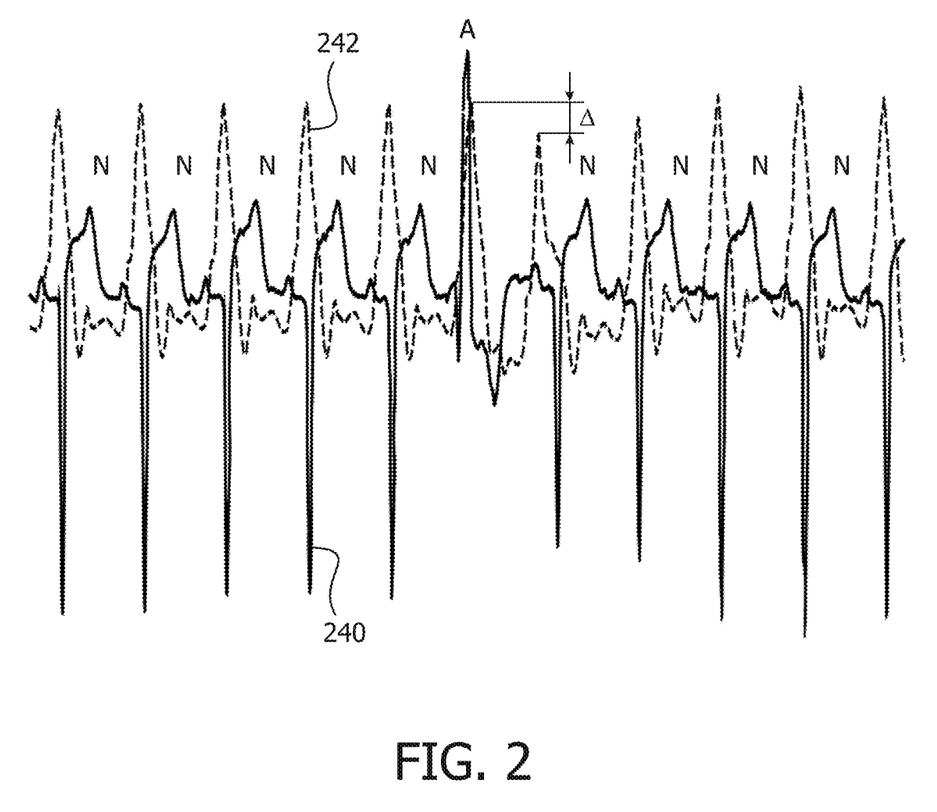
FIG. 2 depicts example waveforms that may be analyzed in accordance with various embodiments.

Referring now to FIG. 2, two example waveforms are depicted. A first waveform 240 depicted in solid line represents electrical activity of a patient, e.g., the signal 114 produced by ECG 104. A second waveform 242 depicted in dashed line represents hemodynamic activity in the patient's vascular system, e.g., the signal 116 produced by ABP 106. In this example, five periodic components (left to right) of first waveform 240 in the form of peaks are annotated/classified with the letter "N" to indicate normal electrical activity in the patient's heart, e.g., as determined by initial annotation engine 125. The sixth electrical peak is annotated with the letter "A" to indicate an "artifact" perceived by initial annotation engine 125, e.g., due to a sudden increase in amplitude and/or abrupt decrease in phase. Following the artifact, there are four more periodic components of first waveform classified as normal.

Periodic components of second waveform 242, which in this example take the form of peaks, are causally related to periodic components of first waveform 240. In particular, an electrical pulse (as represented by a peak) in first waveform 240 is followed by a consequent peak in second waveform 242. This is because the electrical pulse in the patient's heart triggers the heart to pump blood, and the peak blood pressure occurs some time interval after the peak electrical pulse. In this example, there are five similar peaks in second waveform 242 with relatively normal and uniform amplitudes, followed by a higher peak, then a lower peak, followed by four more peaks that approach normal peak amplitude.

As indicated at the symbol Δ, there is a difference in ABP measured between the sixth and seventh peaks of second waveform 242, which appears to have been a consequence of the electrical periodic component classified as an "artifact." The fact that the second waveform 242 exhibits this Δ apparently as a result of the so-called "artifact" in first waveform 240 suggests that the artifact is not an artifact at all. Rather, the corresponding abnormality in second waveform 242 demonstrated by Δ suggests a drop in systolic ABP caused by a premature beat, which results in insufficient blood being pumped by the patient's heart into the vascular system. In other words, a physiological abnormal electrical pulse has caused a physiological abnormal hemodynamic pulse. Using techniques described herein, the periodic component of second waveform 242 indicated at Δ may be classified as "abnormal." In some embodiments, the periodic component (i.e. electrical pulse) of first waveform 240 initially classified as an "artifact" may be reclassified as "abnormal. Then, features of one or both periodic components may be included with templates added to various databases.

Figure 3:
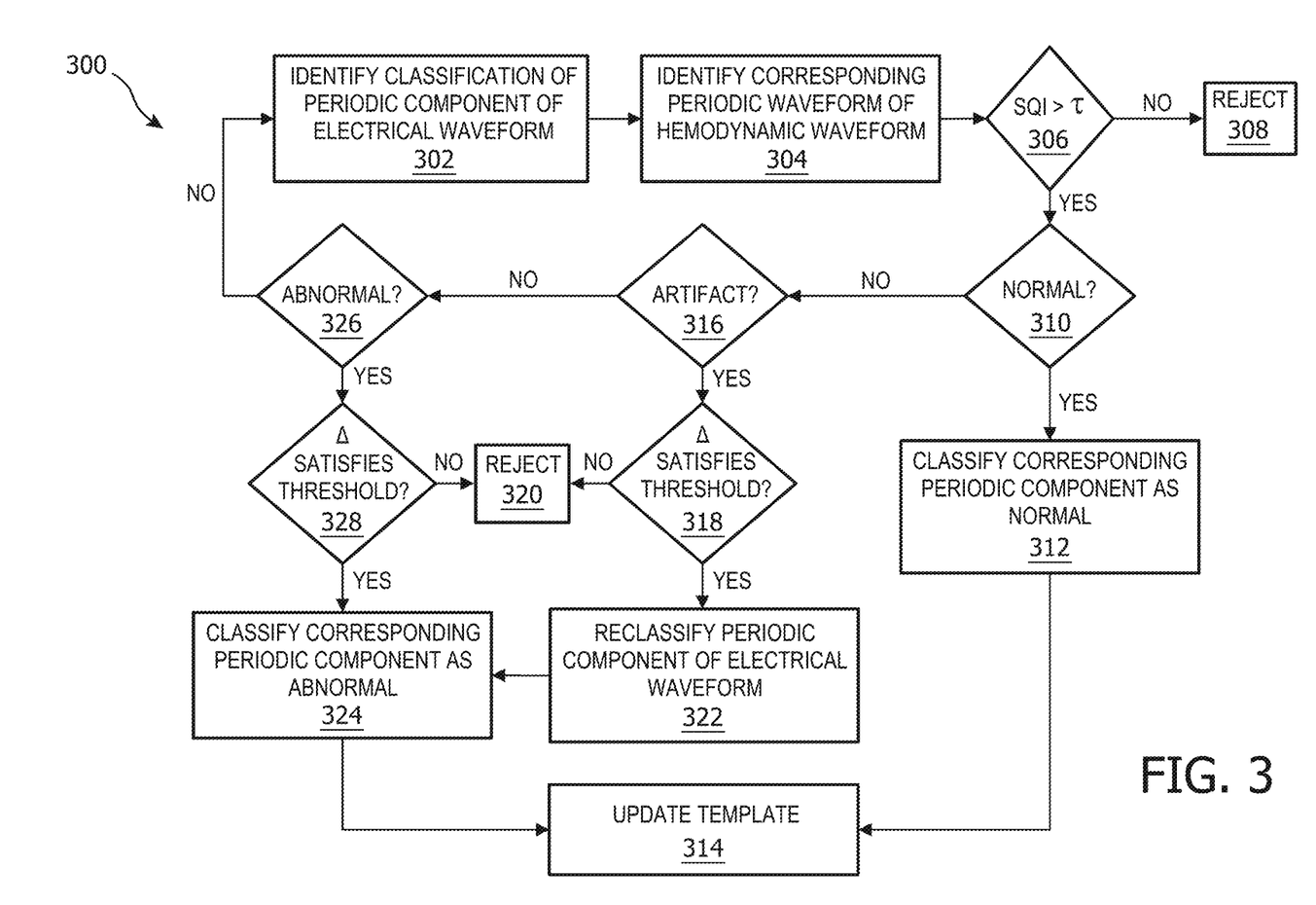
FIG. 3 and FIG. 4 depict example methods in accordance with various embodiments.

FIG. 3 depicts an example method 300 that may be performed by one or more components of cardiovascular analysis system 124, in accordance with various embodiments. In some embodiments, method 300 may be performed initially once a patient is hooked up to one or more health monitoring devices (e.g., 104-112 in FIG. 1) to generate various types of templates (e.g., normal, various categories of abnormal) associated with the patient. In some embodiments, method 300 may cease being performed for the patient when a sufficient number of templates are generated. For example, once there are at least a threshold number of templates having a particular classification (e.g., normal, various types of abnormal), method 300 may no longer be performed unless medical personnel determine that the templates are flawed, in which case they may activate a "relearn" routine which starts template generation for the patient over. While operations of FIG. 3 are depicted in a particular order, this is not meant to be limiting. In various embodiments, one or more operations may reordered, omitted, or added.

At block 302, a classification assigned to a periodic component of an electrical waveform (e.g., signal 114 produced by ECG 104) may be identified. For example, analysis engine 126 may identify an annotation assigned by initial annotation engine 125 to a periodic component in signal 114. Or, analysis engine 126 may analyze a previously-recorded signal waveform with annotations, which may or may not have been added by initial annotation engine 125. At block 304, a corresponding periodic component of a hemodynamic waveform from the same patient may be identified. As mentioned above, the corresponding periodic component may be causally related to the periodic component of the electrical waveform, and in many cases may be identified as corresponding because it trails the electrical periodic component by some predictable time interval or range of time intervals.

At block 306, a signal quality index, or "SQI," of the periodic component of the hemodynamic waveform (or associated with the entire hemodynamic waveform or a portion thereof including multiple periodic components) may be determined. The SQI may be calculated in various ways. In some embodiments, for instance, a SQI associated with an ABP signal may estimate blood pressure at various phases in the cardiac cycle and assign scores based on the physiological plausibility of the signal. Some SQIs may measure morphological normality. Others may measure degradation of the signal due to noise (or artifacts). If the signal represented by the waveform is relatively noisy, that waveform may receive a relatively low SQI. Other SQIs not specifically mentioned herein may be applied as well.

If the SQI determined at block 306 fails to satisfy some threshold τ (which may be, for instance, set to various values), then method 300 may proceed to block 308, at which point the corresponding periodic component of the hemodynamic waveform that was originally identified at block 304 may be rejected. However, if the SQI satisfies the threshold τ, then method may proceed to block 310.

At block 310, it may be determined whether the classification assigned to the periodic component of the electric waveform (which was identified at block 302) is "normal" or some equivalent variation thereof. If the answer is yes, then method 300 may proceed to block 312. At block 312, the corresponding component of the hemodynamic waveform identified at block 304 may be classified as "normal" (or the semantically equivalent variation thereof).

Then, at block 314, one or more features extracted from the now-classified corresponding periodic component may be incorporated into a "normal" hemodynamic template stored in the hemodynamic template database 130. In some embodiments, incorporating the one or features may include coalescing the now-classified corresponding periodic component with a already-coalesced periodic component stored in association with the "normal" hemodynamic template. For example, time durations of the two periodic components may be normalized, and then an average of the two periodic components may be determined.

In some embodiments, a weighted average of the now-classified periodic component with n periodic components represented by the template may be determined. For example, the periodic component of the "normal" hemodynamic template may include an average of the past n periodic components added to the template, each which may or may not be weighted in accordance to how recently they were added. The further back in time a particular periodic component was incorporated into the template (e.g., determined in terms of iterations or pure time), the less weight it may be assigned. Put another way, exponential weights that decrease further in the past may be assigned to the n periodic components that were coalesced into the template. In some embodiments, a low pass filter such as a single pole filter may be employed to determine the periodic component stored in association with the template.

Back at block 310, if the periodic component of the electrical signal was not annotated as "normal," then method 300 may proceed to block 316. At block 316, it may be determined whether the classification assigned to the periodic component of the electric waveform (which was identified at block 302) is "artifact, "noise," or some equivalent variation thereof. If the answer is yes, then method 300 may proceed to block 318. At block 318, it may be determined whether the corresponding periodic component of the hemodynamic waveform satisfies one or more criteria. For example, in some embodiments, it may be determined whether the Δ mentioned previously—that is, the difference between amplitudes between two adjacent peaks—satisfies some threshold. In some embodiments, an equation such as the following may be employed:

$$\Delta = \frac{SBP(n-1) - SBP(n)}{SBP(n-1)} > 5\%$$

wherein SBP(n) is the systolic blood pressure at the periodic component under examination and SBP(n-1) is the systolic blood pressure at the immediately preceding periodic component. While 5% is used as a threshold in this example, it should be understood that this is not meant to be limiting. Various other thresholds may be selected under various circumstances, depending on, among other things, the health of the patient, the circumstances of the patient (e.g., activity in which they are engaged), and so forth.

If the criteria of block 318 are not satisfied, then method 300 may proceed to block 320, at which point the corresponding periodic component may be rejected. This may indicate, for instance, that the periodic component of the electrical waveform was, in fact, properly classified as an artifact. On the other hand, if the criteria of block 318 are satisfied, then method 300 may proceed to block 322. At block 322, the periodic component of the electrical waveform may be reclassified, in this instance from "artifact" to "abnormal." At block 324, the corresponding periodic component of the hemodynamic waveform may likewise be classified as "abnormal." And as was already discussed, at block 314, one or features of the now-classified corresponding periodic component of the hemodynamic waveform may be incorporated into an "abnormal" template stored in the database (e.g., 130).

Back at block 316, if the periodic component of the electrical signal was not annotated as "noise" or an "artifact," then method 300 may proceed to block 326. At block 326, it may be determined whether the classification assigned to the periodic component of the electric waveform (which was identified at block 302) is "abnormal" or some equivalent variation thereof. If the answer is no, then method 300 may proceed back to block 302. However, if the answer at block 326 is yes, then method 300 may proceed to block 328. At block 328, a similar determination may be made as was made at block 318. For example, the same or similar equation as was used above may be used again. If the threshold at block 328 is not satisfied, then method 300 may proceed to block 320, at which point the periodic component of the hemodynamic waveform may be rejected. If the threshold at block 328 is satisfied, then method 300 may proceed to block 324 and then block 314, which were described above.

In FIG. 3, a single SQI determination is made at block 306, but this is not meant to be limiting. In various embodiments, different SQI determinations may be made depending on the classification assigned to the periodic component of the electrical waveform. For example, if it is classified as normal, a first SQI may be determined. If it is classified as abnormal, a second SQI may be determined. And so on. And while the particular equation described above may be used to determine abnormality in a hemodynamic waveform, that is not meant to suggest that it can only be used in isolation, or that alternative equations cannot be used.

Figure 4:
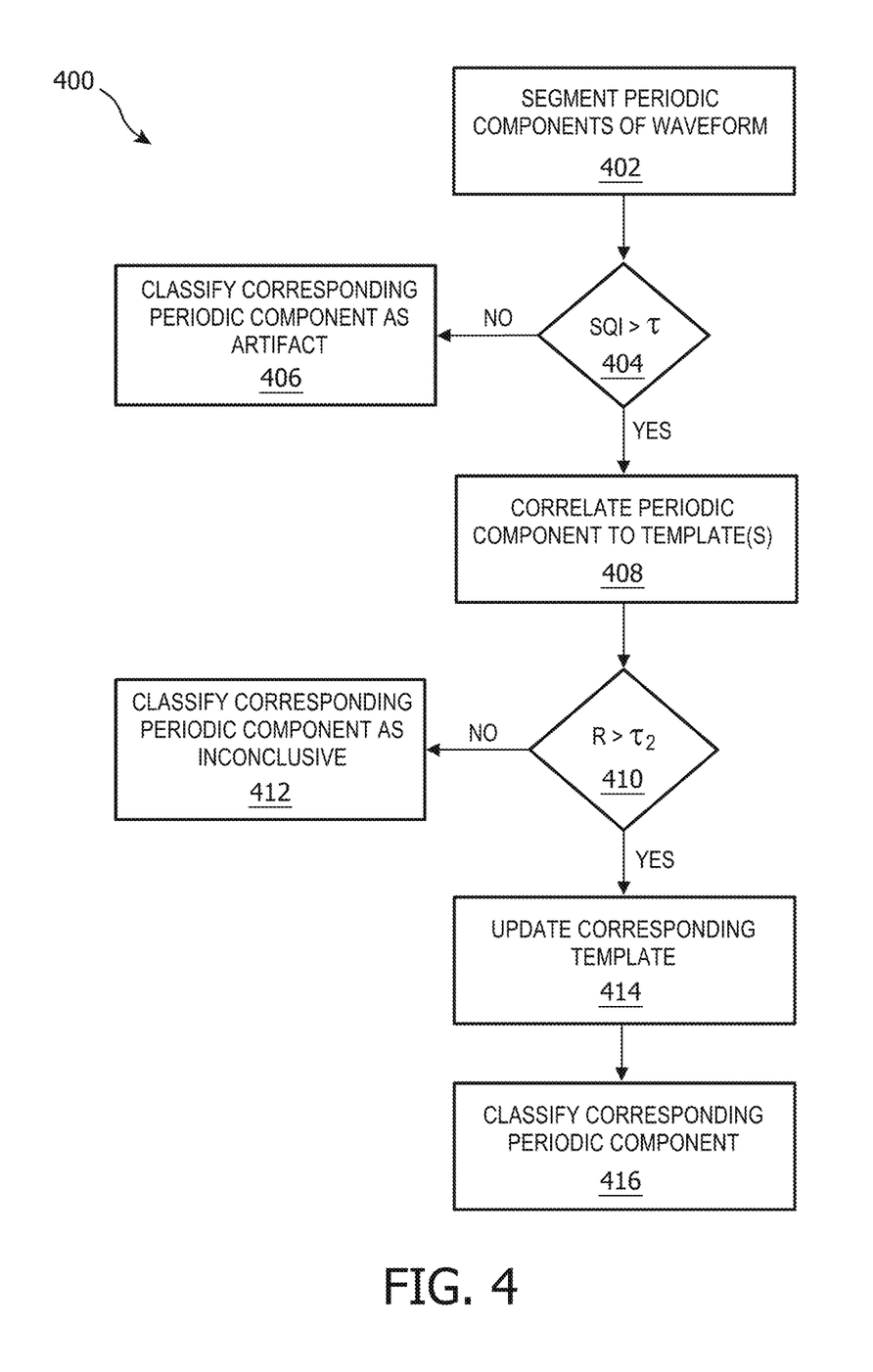

FIG. 4 depicts an example method 400 for using the templates developed using methods such as that depicted in FIG. 3 to classify unclassified periodic waveform components, as well as for continuing to add hemodynamic templates to one or more databases, such as 130. As was the case with method 300, while operations of FIG. 4 are depicted in a particular order, this is not meant to be limiting. In various embodiments, one or more operations may reordered, omitted, or added.

At block 402, the hemodynamic waveform under consideration may be segmented, e.g., into segments that each includes a periodic component such as a peak and/or a valley. At block 404, a SQI may be determined for each segment (or the waveform as a whole), similar to block 306 of FIG. 3. If the SQI fails to satisfy a threshold τ, then method 400 may proceed to block 406, at which point the segment (i.e. a portion of the waveform containing a periodic component) may be classified as "noise" or an "artifact." If the threshold is satisfied, however, then method 400 may proceed to block 408.

At block 408, each segment/periodic component may be correlated to templates in a template databases (e.g., 130). For example, in some embodiments, the segment/periodic component may be correlated to both a normal template and a plurality of abnormal templates, each associated with a different type of abnormal classification (e.g., premature beat, atrial fibrillation, etc.). In some embodiments, and as was mentioned previously, the segment/periodic component under analysis may be subtracted from the template periodic component(s), and the difference may be compared to the one or more thresholds. In other embodiments, techniques such as FFTs or covariance shifting may be employed to correlate the periodic component under analysis to one or more template periodic components.

If at block 410 the correlation R between the segment/periodic component and one or more templates fails to satisfy another threshold ($\tau_2$ in FIG. 4), then method 400 may proceed to block 412, at which point the periodic component may be classified as inconclusive and/or rejected. If the threshold $\tau_2$ is satisfied, however, then method 400 may proceed to block 414. In various embodiments, $\tau_2$ may be an adjustable threshold for evaluating a correlation between the template the segment/periodic component. In some embodiments, $\tau_2$ may set to values between 0.5 and 1, such as 0.8. In other embodiments, $\tau_2$ may be learned over time from patient data (e.g., using machine learning techniques or various heuristics). For example, as more templates are added to the template database, it may be possible to obtain closer matches, and hence $\tau_2$ may change over time.

At block 414, one or more features of the segment (i.e. periodic component) may be incorporated into a template stored in a template databases (e.g., 130). Examples of how periodic components may be incorporated into a template were described above with respect to block 314. At block 416, the segment/periodic component may be classified accordingly, e.g., for use by one or more downstream components and/or algorithms.

Waveforms having their periodic components classified/reclassified/annotated using techniques described herein may be used for various downstream purposes. For example, a periodic component of a hemodynamic waveform such as a peak that is classified as abnormal using techniques described herein may be used to detect and alert hemodynamic deterioration. Additionally, other cardiovascular measurements may be made more accurate when viewed in conjunction with annotated periodic components. For example, heart rate turbulence may be more accurately identified based at least in part on classifications/annotations determined using disclosed techniques. In some embodiments, techniques described herein may be used with sleep monitoring systems that simultaneously monitor ECG and PLETH signals. Additionally, hemodynamic waveforms annotated using techniques here may be used for applications such as clinical decision support algorithms, e.g., to reduce false alarm rates by properly classifying periodic components as abnormalities. As another example, techniques described herein may be used to retroactively correct ECG artifacts in ECG signals as abnormal.

Figure 5:
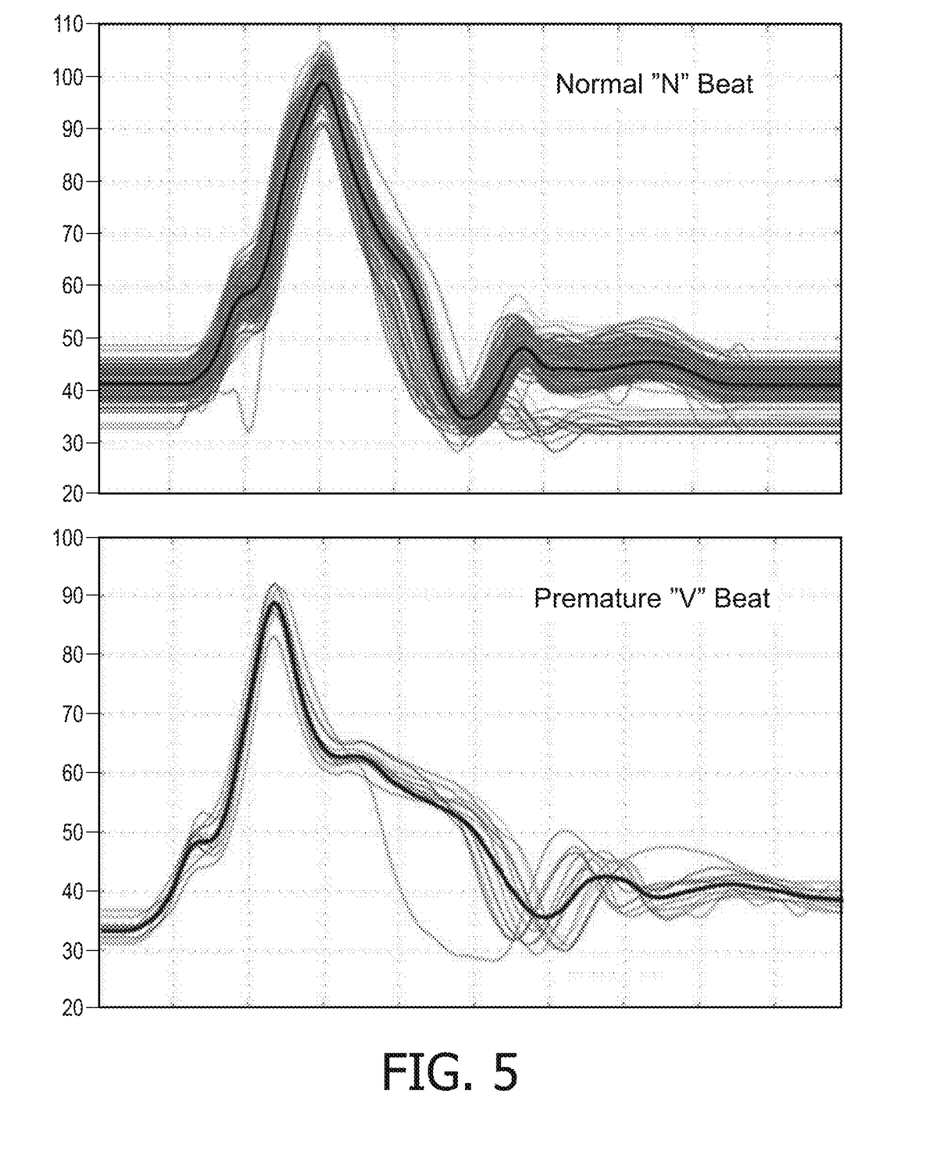
FIG. 5 depicts example "normal" and "abnormal" templates, in accordance with various embodiments.

FIG. 5 depicts non-limiting examples of how multiple accumulated periodic components (referred to in the image as "beats") that have been classified as "normal" (top) and "premature" (bottom, i.e., a particular type of abnormality) may be coalesced into a single cumulative periodic component represented by the bold black line. If an unclassified periodic component is sufficiently similar to those bold-black-line periodic components depicted in FIG. 5, it may be classified accordingly. For example, if a similarity score between a feature vector extracted from an unclassified periodic component and a feature vector extracted from the coalesced cumulative periodic component shown in FIG. 5 satisfies one or more thresholds, that unclassified periodic component may be classified the same.

Figure 6:
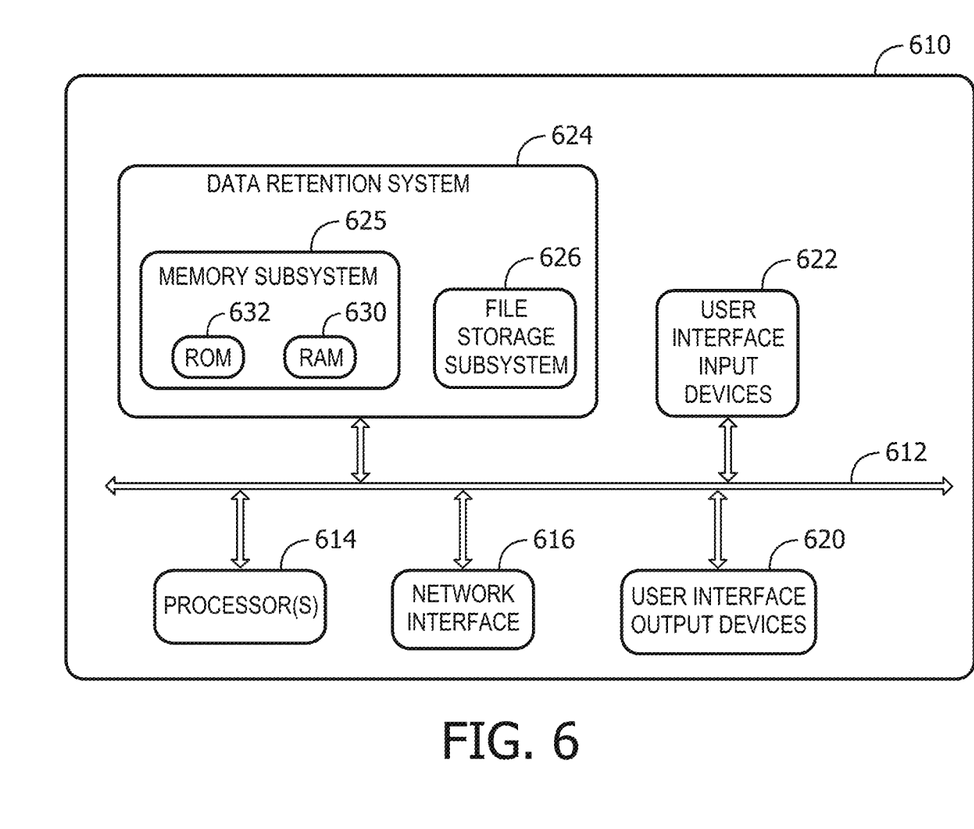
FIG. 6 depicts components of an example computer system.

FIG. 6 is a block diagram of an example computer system 610. Computer system 610 typically includes at least one processor 614 which communicates with a number of peripheral devices via bus subsystem 612. As used herein, the term "processor" will be understood to encompass various devices capable of performing the various functionalities attributed to the CDS system described herein such as, for example, microprocessors, FPGAs, ASICs, other similar devices, and combinations thereof. These peripheral devices may include a data retention subsystem 624, including, for example, a memory subsystem 625 and a file storage subsystem 626, user interface output devices 620, user interface input devices 622, and a network interface subsystem 616. The input and output devices allow user interaction with computer system 610. Network interface subsystem 616 provides an interface to outside networks and is coupled to corresponding interface devices in other computer systems.

User interface input devices 622 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 610 or onto a communication network.

User interface output devices 620 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 610 to the user or to another machine or computer system.

Data retention system 624 stores programming and data constructs that provide the functionality of some or all of the modules described herein. For example, the data retention system 624 may include the logic to perform selected aspects of methods 300 or 400, and/or to implement one or more components of cardiovascular analysis system 124.

These software modules are generally executed by processor 614 alone or in combination with other processors. Memory 625 used in the storage subsystem can include a number of memories including a main random access memory (RAM) 630 for storage of instructions and data during program execution, a read only memory (ROM) 632 in which fixed instructions are stored, and other types of memories such as instruction/data caches (which may additionally or alternatively be integral with at least one processor 614). A file storage subsystem 626 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 626 in the data retention system 624, or in other machines accessible by the processor(s) 614. As used herein, the term "non-transitory computer-readable medium" will be understood to encompass both volatile memory (e.g. DRAM and SRAM) and non-volatile memory (e.g. flash memory, magnetic storage, and optical storage) but to exclude transitory signals.

Bus subsystem 612 provides a mechanism for letting the various components and subsystems of computer system 610 communicate with each other as intended. Although bus subsystem 612 is shown schematically as a single bus, alternative implementations of the bus subsystem may use multiple busses.

Computer system 610 can be of varying types including a workstation, server, computing cluster, blade server, server farm, or any other data processing system or computing device. In some embodiments, computer system 610 may be implemented within a cloud computing environment. Due to the ever-changing nature of computers and networks, the description of computer system 610 depicted in FIG. 6 is intended only as a specific example for purposes of illustrating some implementations. Many other configurations of computer system 610 are possible having more or fewer components than the computer system depicted in FIG. 6.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope

The invention claimed is:

1. A computer-implemented method, comprising:
identifying, by one or more processors, a periodic component of an electrical waveform and a previously-assigned classification associated with the periodic component of the electrical waveform, wherein the electrical waveform represents electrical activity in a patient's heart;
analyzing, by one or more of the processors, a corresponding periodic component of a hemodynamic waveform that represents hemodynamic activity in the patient's cardiovascular system, wherein the corresponding periodic component is causally related to the periodic component of the electrical waveform;
classifying, by one or more of the processors, the corresponding periodic component of the hemodynamic waveform with the previously-assigned classification in response to a determination, based on the analyzing, that the previously-assigned classification also applies to the corresponding periodic component;

identifying, by one or more of the processors, an artifact classification assigned to another periodic component of the electrical waveform deemed an artifact;

analyzing, by one or more of the processors, another corresponding periodic component of the hemodynamic waveform that is causally related to the another periodic component of the electrical waveform;

classifying, by one or more of the processors, the another corresponding periodic component of the hemodynamic waveform with one or more classifications in response to a determination, based on the analyzing, that a delta between the another corresponding periodic component of the hemodynamic waveform and another previous periodic component of the hemodynamic waveform satisfies a threshold;

reclassifying, by one or more of the processors, the another periodic component of the electrical waveform with the one or more classifications; and updating, by one or more of the processors, in a database of hemodynamic templates, a hemodynamic template associated with the previously-assigned classification to include one or more features of the corresponding periodic component of the hemodynamic waveform.

2. The computer-implemented method of claim 1, further comprising receiving, by one or more of the processors, electrophysiological data associated with the patient, wherein the electrophysiological data includes the electrical waveform and one or more previously-assigned classifications associated with one or more periodic components of the electrical waveform; and receiving, by one or more of the processors, hemodynamic data associated with the patient, wherein the hemodynamic data includes the hemodynamic waveform.

3. The computer-implemented method of claim 2, wherein the electrophysiological data is received from one or more electrodes of an electrocardiogram.

4. The computer-implemented method of claim 2, wherein the hemodynamic data comprises a signal indicative of at least one of arterial blood pressure of the patient, pulmonary blood pressure of the patient, and central venous pressure.

5. The computer-implemented method of claim 2, wherein the hemodynamic data comprises a signal from a plethysmograph.

6. The computer-implemented method of claim 1, further comprising:

identifying, by one or more of the processors, an unclassified periodic component of the same hemodynamic waveform or a different hemodynamic waveform associated with a different patient;

matching, by one or more of the processors, the unclassified periodic component to a template of the database of hemodynamic templates; and classifying, by one or more of the processors, the unclassified periodic component of the hemodynamic waveform with a classification associated with the matching template.

7. The computer-implemented method of claim 6, further comprising updating, by one or more of the processors, the matching template to include one or more features of the now-classified periodic component of the hemodynamic waveform.

8. The computer-implemented method of claim 1, wherein the previously-assigned classification comprises an abnormal classification, and wherein the assigning comprises assigning the abnormal classification to the corresponding periodic component of the hemodynamic waveform in response to a determination, based on the analysis, that a delta between the corresponding periodic component of the hemodynamic waveform and a previous periodic component of the hemodynamic waveform satisfies a threshold.

9. The computer-implemented method of claim 1, wherein the previously-assigned classification comprises a normal classification, and wherein the assigning comprises assigning the normal classification to the corresponding periodic component of the hemodynamic waveform in response to a determination, based on the analyzing, that the corresponding periodic component satisfies a signal quality index ("SQI").

10. The computer-implemented method of claim 1, wherein the analyzing comprises matching the corresponding periodic component to a template of the database of hemodynamic templates.

11. The computer-implemented method of claim 10, wherein the updating comprises coalescing the corresponding periodic component with a periodic component stored in association with the matching hemodynamic template.

12. The computer-implemented method of claim 1, wherein the previously-assigned classification comprises one of a normal classification, an artifact classification, and an abnormal classification.

13. A system comprising:

one or more computer processors;

one or more computer readable storage devices;

program instructions stored on the one or more computer readable storage devices for execution by at least one of the one or more computer processors, the stored program instructions comprising:

program instructions to identify a periodic component of an electrical waveform and a previously-assigned classification associated with the periodic component of the electrical waveform, wherein the electrical waveform represents electrical activity in a patient's heart;

program instructions to analyze a corresponding periodic component of a hemodynamic waveform that represents hemodynamic activity in the patient's cardiovascular system, wherein the corresponding periodic component is causally related to the periodic component of the electrical waveform;

program instructions to classify the corresponding periodic component of the hemodynamic waveform with the previously-assigned classification in response to a determination, based on the analyzing, that the previously-assigned classification also applies to the corresponding periodic component;

program instructions to identify an artifact classification assigned to another periodic component of the electrical waveform deemed an artifact;

program instructions to analyze another corresponding periodic component of the hemodynamic waveform that is causally related to the another periodic component of the electrical waveform;

program instructions to classify the another corresponding periodic component of the hemodynamic waveform with one or more classifications in response to a determination, based on the analyzing, that a delta between the another corresponding periodic component of the hemodynamic waveform and another previous periodic component of the hemodynamic waveform satisfies a threshold;

program instructions to reclassify the another periodic component of the electrical waveform with the one or more classifications; and program instructions to update in a database of hemodynamic templates, a hemodynamic template associated with the previously-assigned classification to include one or more features of the corresponding periodic component of the hemodynamic waveform.

\* \* \* \* \*